(12) United States Patent
Riedel

(10) Patent No.: US 11,257,345 B2
(45) Date of Patent: Feb. 22, 2022

(54) METHOD AND DEVICE FOR MONITORING THE ATTENTIVENESS OF AN OPERATING PERSON

(71) Applicant: Smiths Detection Germany GmbH, Wiesbaden (DE)

(72) Inventor: Ulrich Riedel, Mainz-Kastel (DE)

(73) Assignee: SMITHS DETECTION GERMANY GMBH, Wiesbaden (DE)

( * ) Notice: Subject to any disclaimer, the term of this patent is extended or adjusted under 35 U.S.C. 154(b) by 0 days.

(21) Appl. No.: 15/309,740

(22) PCT Filed: May 8, 2015

(86) PCT No.: PCT/EP2015/060214
§ 371 (c)(1),
(2) Date: Nov. 8, 2016

(87) PCT Pub. No.: WO2015/169954
PCT Pub. Date: Nov. 12, 2015

(65) Prior Publication Data
US 2017/0270764 A1    Sep. 21, 2017

(30) Foreign Application Priority Data

May 9, 2014  (DE) .......................... 102014208711.2

(51) Int. Cl.
*G08B 21/04* (2006.01)
*G08B 21/06* (2006.01)
(Continued)

(52) U.S. Cl.
CPC ............ *G08B 21/0415* (2013.01); *A61B 5/18* (2013.01); *G01V 5/0016* (2013.01);
(Continued)

(58) Field of Classification Search
None
See application file for complete search history.

(56) References Cited

U.S. PATENT DOCUMENTS 4,755,140 A * 7/1988 Rimland ................ A61B 5/162
273/446
4,770,636 A * 9/1988 Buschke ................. G09B 7/02
273/273
(Continued)

FOREIGN PATENT DOCUMENTS

DE    102005030934 A1    1/2007
DE    102008050542 A1    4/2010
(Continued)

OTHER PUBLICATIONS

International Search Report dated Sep. 21, 2015 for PCT/EP2015/060214.
(Continued)

*Primary Examiner* — Catherine T. Rastovski
*Assistant Examiner* — Leonard S Liang
(74) *Attorney, Agent, or Firm* — Kevin E. West; Advent, LLP

(57) ABSTRACT

The invention relates to a method and corresponding devices for monitoring the attention of an operator of an X-ray inspection system for nondestructive inspection of inspection objects and for ensuring the presence and/or attention of an operator of the X-ray inspection system including the following steps: display of a piece of information that defines a randomly determined desired input; detection of an actual input of the operator as a response to the displayed desired input; and, based on the desired input and the actual input, determination of a signal that indicates the attention of the operator.

12 Claims, 4 Drawing Sheets

(51) Int. Cl.
*G01V 5/00* (2006.01)
*G06F 3/0488* (2013.01)
*G06Q 50/26* (2012.01)
*A61B 5/18* (2006.01)
*G06F 3/04886* (2022.01)
*G06F 3/0484* (2013.01)
*G06F 3/04842* (2022.01)

(52) U.S. Cl.
CPC ......... *G06F 3/04886* (2013.01); *G08B 21/06* (2013.01); *G06F 3/0488* (2013.01); *G06F 3/04842* (2013.01); *G06Q 50/265* (2013.01)

(56) References Cited

U.S. PATENT DOCUMENTS

| | | | | |
|---|---|---|---|---|
| 4,978,303 A * | 12/1990 | Lampbell | | G09B 19/00 273/445 |
| 5,012,226 A * | 4/1991 | Love | | B60K 28/066 180/272 |
| 5,079,726 A * | 1/1992 | Keller | | G09B 19/00 273/446 |
| 5,392,030 A | 2/1995 | Adams | | |
| 5,585,785 A | 12/1996 | Gwin et al. | | |
| 6,113,538 A * | 9/2000 | Bowles | | A61B 5/16 600/300 |
| 6,899,540 B1 * | 5/2005 | Neiderman | | G09B 7/00 434/219 |
| 7,257,189 B2 * | 8/2007 | Modica | | G01V 5/0008 378/210 |
| 7,903,783 B2 * | 3/2011 | Modica | | G09B 5/00 378/57 |
| 7,952,566 B2 * | 5/2011 | Poupyrev | | G06F 3/016 345/173 |
| 8,869,261 B1 * | 10/2014 | Carter | | G06F 3/04886 726/14 |
| 9,131,123 B2 * | 9/2015 | Ichikawa | | G08G 1/167 |
| 2003/0023592 A1 * | 1/2003 | Modica | | G09B 19/00 |
| 2003/0095046 A1 | 5/2003 | Borugian | | |
| 2005/0192513 A1 | 9/2005 | Darby et al. | | |
| 2007/0166675 A1 * | 7/2007 | Atkins | | G09B 7/00 434/236 |
| 2008/0044801 A1 * | 2/2008 | Modica | | G06Q 10/06398 434/307 R |
| 2008/0260096 A1 * | 10/2008 | Sommer | | G01V 5/0016 378/57 |
| 2009/0267777 A1 * | 10/2009 | Kumar | | G08B 21/06 340/576 |
| 2011/0051996 A1 * | 3/2011 | Gudmundson | | G06T 7/60 382/100 |
| 2011/0102142 A1 * | 5/2011 | Widger | | H04N 7/18 340/5.83 |
| 2012/0187312 A1 * | 7/2012 | Guez | | A44C 5/20 250/492.1 |
| 2012/0236996 A1 * | 9/2012 | Guez | | A44C 5/20 378/117 |
| 2012/0278766 A1 * | 11/2012 | Massengill | | A61B 3/113 715/846 |
| 2012/0310117 A1 * | 12/2012 | Teicher | | A61B 5/165 600/595 |
| 2013/0135109 A1 * | 5/2013 | Sharon | | G08B 21/02 340/576 |

FOREIGN PATENT DOCUMENTS

| | | |
|---|---|---|
| DE | 102010022433 A1 | 12/2011 |
| DE | 102013207143 A1 | 11/2013 |
| WO | WO-2006119629 A1 * | 11/2006 ............ G06Q 50/30 |
| WO | 2013187874 A1 | 12/2013 |

OTHER PUBLICATIONS

International Preliminary Report on Patentability dated Nov. 15, 2016 for PCT/EP2015/060214.

* cited by examiner

METHOD AND DEVICE FOR MONITORING THE ATTENTIVENESS OF AN OPERATING PERSON

The present disclosure generally relates to the field of safety devices for systems or machines, which as they operate, must be monitored by an operator. In particular, the present disclosure relates to a method and device for monitoring the attention of an operator.

BACKGROUND

There are several safety devices that take the form of a dead man's control. For example, there are X-ray systems in which, for safety reasons, a dead man's control must be actuated when an adjustment to the device is carried out. In some devices, a touch screen with a pressure-sensor unit as an operator interface for an industrial technical device that has a handle equipped with an actuating element, which is connected in a signal-carrying fashion to an evaluation unit, and an actuation of the actuating element is evaluated by the evaluation unit in addition to an exertion of pressure on the region of the touch screen so that for example, an activation of drive units only takes place if the actuating element is also actuated. Some motor vehicles use a pushbutton, which a driver must actuate periodically or when requested in order to be able to detect driver fatigue.

These safety devices, however, are essentially limited to checking for the physical presence or physical integrity of an operator. Specifically when an operator works with a system or machine for a longer period of time, despite the requirement to actuate the safety device at irregular intervals, the operator can get into a certain routine, which can result in the fact that the operator actuates the safety device unconsciously. Consequently, these safety devices do in fact fulfill their primary purpose, but can neither ensure nor monitor the attention of the operator that is required for safety reasons.

Further, some interactive alarm systems ensure that a person, such as an aircraft pilot, a truck driver, a soldier or sailor on sentry duty, or safety personnel remains alert, i.e. is not dozing, sleeping, or even unconscious. The alarm system gives a person instructions and time to input a code, and alerts the person or a third party if the code is not promptly and correctly input.

Some vehicles have implemented a device and a method for checking the capacities of a driver to drive the vehicle by showing the driver a random code on a display for a certain period of time, which the driver must correctly input within a certain amount of time.

SUMMARY

The present disclosure proposes a method and device, which, in addition to checking for the presence of an operator of an X-ray inspection system for nondestructive inspection of inspection objects, is also suitable for monitoring the operator's attention.

Features and details that are described in connection with the method according to the present disclosure naturally also apply in connection with the device according to the present disclosure and vice versa. For this reason, reciprocal reference is made with regard to the disclosure of the individual aspects.

The present disclosure is directed to safety devices in the form of a dead man's control wherein an actuation of the safety device requires a certain amount of attention on the part of the operator. The present disclosure essentially proposes modifying the dead man's control principle such that the actuation of the safety device cannot become routine in that when actuating the safety device, the operator must take into account a randomly generated piece of information as an input requirement so that the actuation is interpreted by the safety device as the correct response. This prevents the safety device from being routinely actuated more or less unconsciously. The method according to the present disclosure and the device according to the present disclosure overcome precisely this weakness of the safety devices described above.

A first aspect of the present disclosure relates to a method for monitoring the attention of an operator of an X-ray inspection system for nondestructive inspection of inspection objects and for ensuring the presence and/or attention of an operator of the X-ray inspection system, having the following steps: display of a piece of information (or input instruction), which defines a randomly established desired input; detection of an actual input of the operator as a response to the displayed desired input; and establishment or generation—based on the desired input and actual input—of a signal that is representative of the attention of the operator.

Because the operator cannot know the "correct" response or actuation of the safety device in advance, this ensures that the operator must take note—with the necessary degree of attention—of the displayed information (or input instruction) in order to correctly actuate the safety device. In other words, the operator only knows the "correct" response if he has consciously, i.e. attentively, perceived the displayed information.

In this connection, a determination can be made as to whether a current actual input by the operator occurs within a predetermined time interval once the information has been displayed. The predetermined time interval, which defines a time window within which the operator must perform the actuation, also makes it possible to detect and ensure the responsiveness of the operator as an additional measure of his attention. In addition, the time interval clearly establishes a time after which no input by the operator can be judged an incorrect input.

In a first embodiment, the displayed information defines a randomly determined location on an input device. A region on the input device that the operator touches as a response can then be detected. Based on a comparison of the location on the input device touched by the operator as an actual input with the randomly determined location as the desired input, it is then possible to generate the signal, which is representative for the attention of the operator.

This embodiment is particularly easy to implement by means of software for example on machines or systems that, like a personal computer, are equipped with a screen as a display unit and a keyboard as an input device. For example, the layout of the keyboard can be displayed on the screen. A key that has been randomly selected by a random generator can be displayed to the operator graphically, for example according to the present disclosure by means of a different color or by means of flashing (color change and/or intensity change). Alternatively, information identifying the key that is to be pressed can be shown to the operator in another region of the screen. The key that has been randomly selected and displayed on the screen therefore defines the location on the input device, namely the corresponding key on the keyboard that the operator should press as the "correct" response. Because of the definite distinguishability of the different keys on a keyboard, it is possible to evaluate the actual input digitally in the sense of true/false.

Another implementation is possible if the display device and input device can be combined, for example in a touch-sensitive screen (touch screen). It is then possible to display a keyboard, a numeric keypad, or symbols arbitrarily distributed on the display surface. As in the description above, a randomly selected location can be displayed with colors, flashing, or some other indication. In other words, a layout of a keyboard could once again be shown on the display unit. Then a randomly selected key is shown to the operator in a graphically highlighted way. Alternatively, it is also possible in this case for information identifying the key that is to be pressed to be shown to the operator in a different region of the screen. In order to input a response, it is then necessary for the operator to touch the location previously defined on the display unit. This establishes the actual input.

Alternatively, it is possible to identify or highlight a randomly determined location on the touch-sensitive screen (touch screen) in order to define the actuation location on the display as the desired input. In other words, the identified location then constitutes the information (or input instruction). This can be graphically depicted on the touch screen, for example, by displaying an X, a dot, or a circle, or in some other way. The desired input is thus visibly displayed for the operator as the location on the display unit. In order to input a response, the operator only has to touch the identified location on the touch screen. This establishes the actual input.

The above embodiments can be modified as follows. In a first time interval, the operator is first shown the randomly determined information, which defines the desired input. After the first time interval expires, the information is no longer displayed and then the time interval begins in which the operator's input is detected. In this embodiment, the operator must pay even more attention since at the time that the response is being input, the information (input instruction) that defines the "correct" response is no longer being displayed. The desired input must be remembered, so to speak. This prevents the touching of a marked location from becoming routine for the operator.

The above explanations can also be combined in a device in a randomly alternating fashion. The resulting variety achieved for the operator likewise requires attention.

In an alternative embodiment, the information (or input instruction), which defines a randomly determined desired input may be a randomly determined desired value. This value can be displayed to the operator quantitatively in a graphic and/or alphanumeric fashion on the display unit. In order to input a response, the operator then actuates the input element. The input element may be configured so that the current actuation can be uniquely assigned to an actual value. This actual value then may establish the actual input, for example at the end of the predetermined time interval for the input. The actual input can then once again be compared to the desired value as the desired input and based on this comparison, the signal, which is representative for the attention of the operator, can be generated.

The input element may be configured so that the current actuation can be uniquely assigned to an actual value. This actual value then may establish the actual input, for example at the end of the predetermined time interval for the input. The actual input can then once again be compared to the desired value as the desired input and based on this, the signal, which is representative for the attention of the operator, can be generated.

The quantitative graphic display can, for example, be graphically displayed on the display unit in an analog, i.e. continuous, fashion or in a discrete, i.e. stepped, for example segmented, fashion, in the form of (continuous or segmented) bars of different lengths, or in a fashion similar to a pointer display instrument.

In a modification of this embodiment, a current actual value that may be derived from the actuation of the input element by the operator can likewise be graphically displayed for the operator as feedback on the display unit, which may be done in the same way as the information is displayed. The graphic or alphanumeric display of the currently derived actual value thus achieved assists the operator in the form of feedback for the inputting of the "correct" response.

The above embodiment can also be modified by adding a touch-sensitive screen (touch screen) in accordance with the embodiments described above. The randomly determined desired value in this case may once again be shown to the operator quantitatively in a graphic and/or alphanumeric fashion on the touch screen. In order to input a response, the operator then can touch the touch screen functioning as an input element. In order to control the input, the operator can then influence another quantitative graphic display on the touch screen with a finger by executing a gesture such as a swiping or dragging on the surface of the touch screen. The quantitative graphic display, like the information, which may define the randomly determined desired input, can be graphically depicted on the display unit in an analog, i.e. continuous, fashion or in a discrete, i.e. stepped, for example segmented, fashion, in the form of (continuous or segmented) bars of different lengths, or in a fashion similar to a pointer display instrument. An actual value that may be derived from the currently executed input by the operator by means of the gesture on the touch screen is then graphically shown to the operator at the same time as feedback on the touch screen in the same way as the information. The display of the currently derived actual value achieved in this way offers the operator assistance in the form of feedback for inputting the "correct" response.

In the above embodiments with feedback, actuation of the safety device by the operator requires the operator to interact with the safety device for a certain amount of time and therefore makes it possible to provide even better assurance that the operator is devoting his complete attention to the safety device and thus to the machine or system.

In this embodiment, it is also possible to work with two time intervals, with a first time interval being initially provided in which the operator is given the opportunity to actuate the input element or touch screen. The current actual value produced by the actuation is preferably shown to the operator quantitatively in a graphic and/or alphanumeric fashion on the display unit or touch screen. The operator is therefore provided with the above-described feedback based on which he can correct the input. In a subsequent time interval, the operator is likewise shown, preferably optically, that the second time interval has begun, at the end of which the current actual value is evaluated, i.e. is detected as an input.

In all of the above-described embodiments, in addition to the optical display of the randomly determined information, it is also possible to signal the operator acoustically and/or haptically that an attention check is being performed. An acoustic signaling can, for example, be achieved by playing a sound that is uniquely assigned to the function over a speaker. A haptic signaling can, for example, be carried by means of a vibration unit, which can be integrated, for example, into an item of clothing or armband, etc. worn by the operator and/or integrated into the surface of a seat.

A second aspect of the present disclosure essentially relates to a device configured in accordance with the above-discussed method for monitoring the attention of an operator of an X-ray inspection system for nondestructive inspection of inspection objects and for ensuring the presence and/or attention of an operator of the X-ray inspection system. The device accordingly includes the following: a processing unit configured to generate information (in the form of an input instruction), which defines a randomly determined desired input; a display unit for displaying the information; and an input device for detecting an actual input of the operator as a response to the displayed desired input; in which the processing unit is operatively coupled to the display unit and input device and is configured to determine a signal, which is representative for the attention of the operator, based on the desired input and the actual input.

Similarly to the method the processing unit may also be configured to determine whether an actual input has occurred within a predetermined time interval since the display of the information began.

According to the first embodiment, the processing unit may be configured to highlight as the information on the display unit a randomly determined location on the input device. A location on the input device that is touched by the operator can then be detected and then, as the actual input, can be compared to the displayed location as the desired input. As explained above in connection with the method according to the present disclosure, the display unit can be a screen and the input device can be a keyboard. The display unit and the input device can also be combined into one unit, as is the case, for example, with a touch-sensitive screen or touch screen.

According to the second embodiment, the processing unit may be configured to display as the information (or input instruction) on the display unit a randomly determined desired value that can be displayed quantitatively in a graphic and/or alphanumeric fashion as the desired input. An actual value may then be derived from an actuation that the operator performs on the input device and then as the actual input, is compared to the desired value as the desired input by the processing unit. The processing unit may also be configured to generate the signal, which is representative for the attention of the operator, based on the comparison result.

The processing unit may also be configured to show the operator an actual value that can currently be derived from the actuation of the input device by the operator, likewise displaying this value quantitatively in a graphic and/or alphanumeric fashion on the display unit in the form of feedback. This offers the operator the possibility of adapting his own actuation of the input device interactively with the information shown on the display unit in order to input a "correct" response The display unit can be a screen that can basically be any kind of display such as an LCD screen, a TFT screen, or the like. The display unit can also be a touch screen.

The input device may be a gradually actuatable actuating element so that based on an actuation of the actuating element performed by the operator, the processing unit is able to derive the actual value as the actual input.

In one embodiment, the actuating element is coupled, for example, to a pressure sensor in such a way that when the actuating element is actuated, values from a predetermined value range for the pressure exerted on the actuating element can be gradually generated.

In other embodiments, the input device can also (as explained above in connection with the method) be implemented with a touch screen, which then also constitutes the display unit; in this case, the input by the operator is then preferably carried out by means of the above-described gesture, for example by swiping or dragging a finger across the surface of the touch screen.

An embodiment of the above-described device can be coupled to a safety device of a system, the reliable operation of which requires not only the presence, but also particularly the attention of an operator, and the safety device can be configured to control the system based on the signal that is representative for the attention of the operator.

For example, the safety device may be configured to bring the system or machine into a safe state; for example, it can properly set the system or machine into a predetermined state. In addition or alternatively, the safety device may be configured to trigger an alarm, which is first intended to arouse the attention of the operator or notify third parties via corresponding communication connections and thus inform them of the error state of the system.

The The methods or devices of the present disclosure may be used in machines or systems whose largely automatic function is supervised or monitored by an operator. The methods or devices of the present disclosure can, however, basically be used in machines and systems in which it is necessary to ensure not only that the operator is fully present, but also particularly to ensure that he is paying attention when monitoring/supervising the machine or system.

BRIEF DESCRIPTION OF THE DRAWINGS

Other advantages, features, and details of the present disclosure ensue from the following description in which embodiments of the present disclosure are described in detail with reference to the drawings. In this connection, the features mentioned in the claims and in the description can each be intrinsically essential to the present disclosure by themselves or in any combination with one another. The features mentioned above and explained again in greater detail here can each be used by themselves or can be used in any combination with one another. Some parts or components that are functionally similar or identical have been provided with the same reference numerals. The terms "left," "right," "top," and "bottom" used in the description of the embodiments refer to the drawings in an orientation in which the figure name and/or reference numerals can be read in the normal way. The embodiments shown and described are understood not to be exhaustive, but instead to have an exemplary character for the explanation of the present disclosure. The detailed description is provided in order to inform the person skilled in the art and therefore the description does not illustrate or explain known circuits, structures, and methods in detail in order not to complicate the comprehension of the present description.

DETAILED DESCRIPTION

Figure 1:
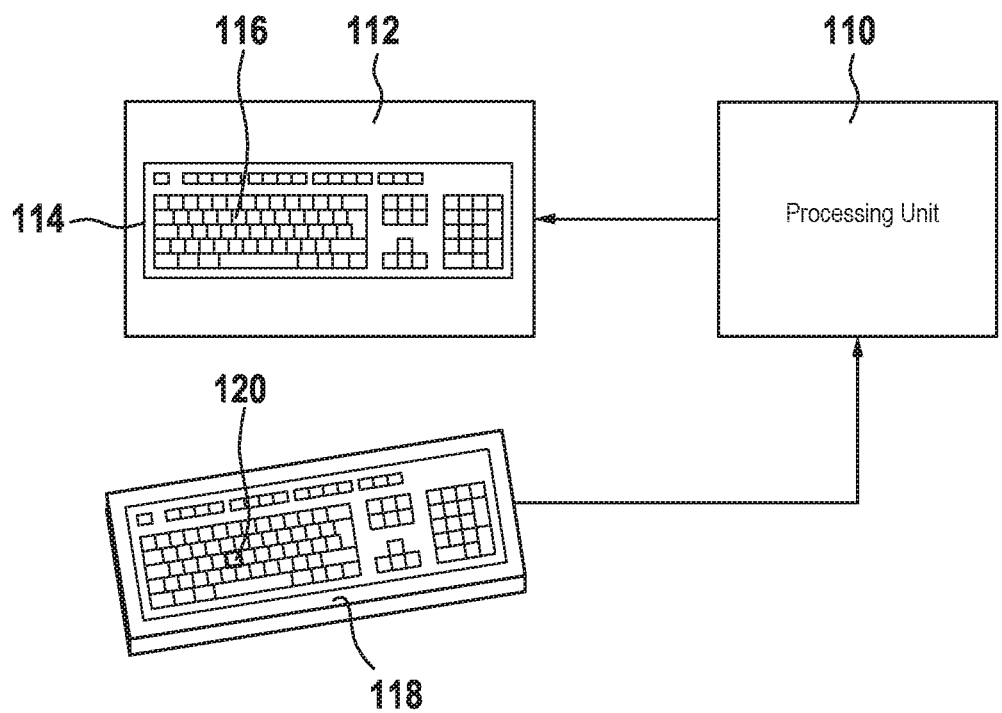
FIG. 1 shows a first embodiment of a monitoring device with a display unit and a separate input device.

FIG. 1 shows a schematic block diagram of a first embodiment of a monitoring device for monitoring the attention of an operator of an apparatus. The apparatus can be a system or a machine whose operation requires the assurance that an operator is paying attention.

A processing unit 110 is connected to a display unit 112 for displaying alphanumeric and graphic information in the way known from computer screens. The display unit can thus be any screen such as an LCD-, TFT-, LED-, OLED-, or plasma screen. The processing unit 110 is also connected to an input device 118, which is a known, commercially available keyboard of the kind known from computer workstations.

In order to implement a method for monitoring the attention of the operator of the apparatus, the processing unit 110 is configured to show the layout of the keyboard, i.e. the input device 118, at irregular intervals on the screen in the form of a graphic representation 114 of the keyboard layout on the display 112.

The processing unit 110 is also configured to generate a piece of information that defines a randomly determined desired input for the operator. To this end, in the present exemplary embodiment, a random generator of the processing unit 110 determines a key of the keyboard layout of the input device 118.

The randomly determined key is displayed on the display unit 112—in the keyboard layout 114 shown there—as a key 116 that is optically highlighted relative to the other keys, for example the "T" key. This randomly determined and optically highlighted key 116 therefore corresponds to the information that is shown to the operator and with which a desired input for the operator is defined. The key 116 can, for example, be optically highlighted by means of a different color or brightness. It is also possible for the key 116 to be marked with a flashing effect, for example in that the color of the key regularly alternates between two or more colors and/or brightness values.

Once the randomly selected key 116 is displayed, a timer in the processing unit 110 is started, which defines a predetermined time window within which the operator must complete an input.

The operator, using the keyboard as an input device 118, can then press the key 116 shown on the display unit 112 in order to confirm that he is paying attention. An input by the operator that is completed within the time window being monitored with the timer, i.e. the pressing of the key 120, corresponds to the actual input by the operator as a response to the displayed desired input. In the case shown, the operator presses the "G" key.

The processing unit 110, which is operatively connected to the display unit 112 and the input device 118, is configured to compare the desired input (in this case the "T" key) on the display unit 112 to the actual input (in this case the "G" key) made by the operator.

If the key shown on the display unit 112 coincides with the key 120 pressed on the input device 118 within the permissible time interval, then the processing unit 110 evaluates this as a positive confirmation by the operator that he is paying attention and generates a corresponding signal that shows that the operator is paying attention.

In the case shown in FIG. 1, the operator has pressed the incorrect key, namely the "G" key instead of the correct key (the "T" key). The processing unit interprets this as an indicator that the operator is not paying attention and generates a corresponding signal indicating operator's attention level. The same conclusion is reached if the operator does not complete an input within the permissible time interval.

The first embodiment is suitable for being implemented solely by software means on already existing workstations of an operator similar to a known computer workstation. The function of the processing unit 110 is particularly easy to integrate in the form of a software routine into the operating system level and the above-described steps for monitoring the attention of the operator are implemented by means of the screen as the display unit and the keyboard as the input device that are present in such a workstation anyway.

Figure 2:
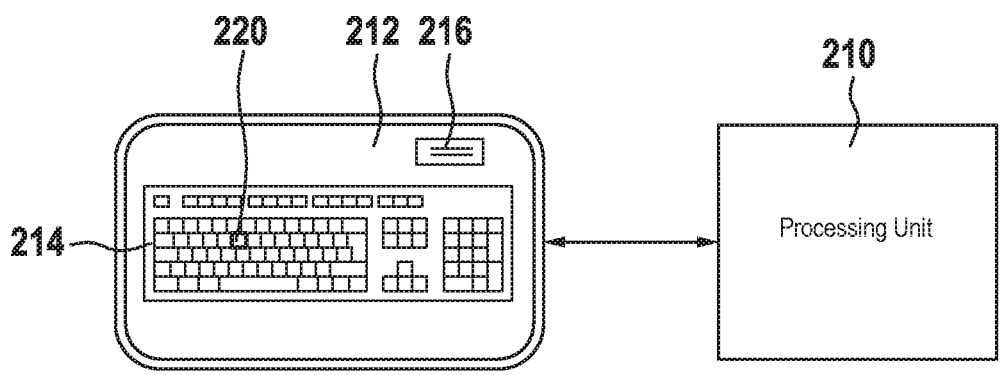
FIG. 2 shows a second embodiment of a monitoring device with a combined display unit/input device in the form of a touch screen.

FIG. 2 shows a second embodiment of the monitoring device, which essentially corresponds to the first embodiment. The essential difference lies in the fact that the display unit and input device are combined in the form of a touch screen 212, i.e. a touch-sensitive screen.

The processing unit 210 is connected to the touch screen 212 serving as a combined display/input device. In order to implement the monitoring of the operator's attention, in this case, analogous to the exemplary embodiment in FIG. 1, a keyboard layout 214 in any graphic form is displayed. In addition to the keyboard layout 214, the processing unit 210 shows a key identification 216—for example "T"—as the information that defines a randomly determined desired input. In other words, the displayed key identification 216 determines the desired input for the operator.

In order to confirm that he is paying attention, the operator is then required, as an input, to touch the surface of the touch screen 212 on the displayed keyboard layout 214 at the location that corresponds to the "T" key.

As discussed in connection with the embodiment in FIG. 1, a key 220, which the operator has identified by touching the touch screen 212 in the keyboard layout 214 with a finger, is then detected by the processing unit 210 and can thus be compared to the randomly determined desired input.

In the example shown, the touching of the key 220 labeled "T," as the actual input of the operator, corresponds to the expected desired input. The processing unit 210 interprets this as a positive indication that the operator is paying attention and correspondingly generates the signal that corresponds to the operator paying attention.

In reverse circumstances, i.e. if the operator does not complete the input on time, does not make an input at all, or touches the incorrect location on the touch screen 212, then the processing unit 210 generates a correspondingly negative signal for the operator's attention.

Figure 3:
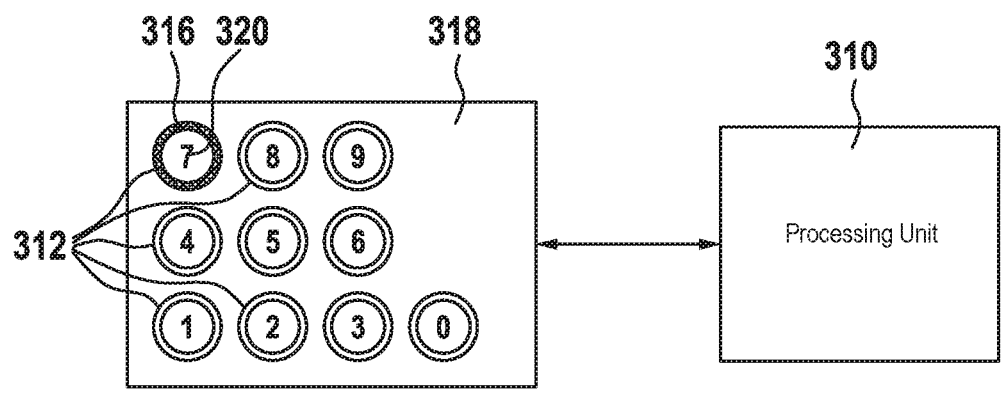
FIG. 3 shows a third embodiment of a monitoring device with an input device in the form of a keypad that has a display element.

FIG. 3 shows a third embodiment for a device for monitoring the attention of an operator. In a modification relative to the first and second embodiments, there is no display unit in the conventional sense. The display unit is configured in the form of display elements that are integrated into a keypad 318 serving as the input device.

For example, the keypad can be a numerical keypad with numbers for the keys 0 through 9. A display element is any key with an illuminated ring 312, which is made of a light-conducting plastic, for example, which can be occasionally illuminated or not by means of an internally installed light source.

The processing unit 310 then uses a random generator to determine one of the keys 0 through 9, for example the key 320 labeled "7," as the randomly determined desired input for the operator. The randomly determined desired input, namely the key 320, is displayed by means of a display element 312 integrated into the keypad 318 in that the ring 316 encompassing the key 320 is illuminated. In other words, the illumination of the ring 316 shows the operator the information that indicates the randomly determined desired input, namely the "7" key.

The operator can then once again—in a way similar to that used in the exemplary embodiments shown in FIGS. 1 and 2—make an input within a predetermined time window by pressing one of the keys on the keypad 318.

Assuming that the operator presses the key 320 in time, this is then detected by the processing unit 310, which is connected to the keypad 318. Correspondingly, the processing unit 310, which is coupled to the display means 312 functioning as the display unit and coupled to the keypad 318 functioning as the input device, can compare the actual input, i.e. the key 320 pressed by the operator, to the desired input, i.e. the displayed key 320. Based on the comparison result, the processing unit 310 then generates the signal that indicates the attention of the operator. In the present case, the operator has been shown the "7" key and the operator has pressed the "7" key within the required time interval so that the processing unit 310 has generated a positive signal for the attention of the operator.

Figure 4:
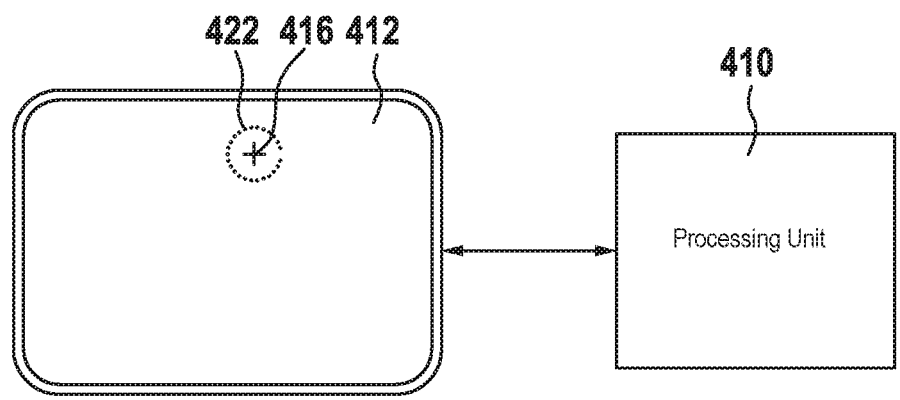
FIG. 4 shows another embodiment of a monitoring device with a touch screen as a combined input/output device.

FIG. 4 shows a fourth embodiment of a device for monitoring the attention of the operator. Similar to the embodiment in FIG. 2, the processing unit 410 is operatively connected to a touch screen 412 functioning as a combined display/input device.

In order to monitor the attention of the operator, the processing unit 410 first randomly generates coordinates of a touchable location on the touch screen 412. These randomly determined coordinates define a location on the touch screen 412 as a randomly determined desired input, which an operator is supposed to touch in order to confirm that he is paying attention.

To show the operator this randomly determined desired input, the processing unit 410 displays the desired input in the form of a symbol 416 appearing at the randomly determined location on the touch screen 412. In the exemplary embodiment, the symbol 416 is an X that identifies the location. This can also be any other symbol, for example a circle, a square, or simply a dot. The symbol should essentially be able to identify a location on the touch screen, which is to be touched, with sufficient precision for the method described here.

Once the symbol 416 is shown on the touch screen 412, the processing unit 410 once again monitors the time window within which the operator is supposed to touch the location on the touch screen 412 that is identified with the symbol 416.

The touch screen 412 simultaneously functioning as a display unit and input device detects the location at which the operator touches the touch screen 412 and reports the coordinates of the location that has been touched back to the processing unit 410. The processing unit 410 compares the coordinates of the desired input to the coordinates of the actual input. Based on the comparison result, the signal representing the attention of the operator is once again generated.

Since the touching of a location on a touch screen 412 cannot be simply evaluated digitally like the actuation of a mechanical key, for example, the processing unit 410 is configured to take into account a certain tolerance range when comparing the actual input to the desired input.

Such a tolerance range is indicated in FIG. 4 by the dashed circle 422 around the symbol 416. In other words, any contact by the operator inside of the circle 422 marked on the touch screen 412 is evaluated by the processing unit 410 as corresponding to the desired input.

Figure 5:
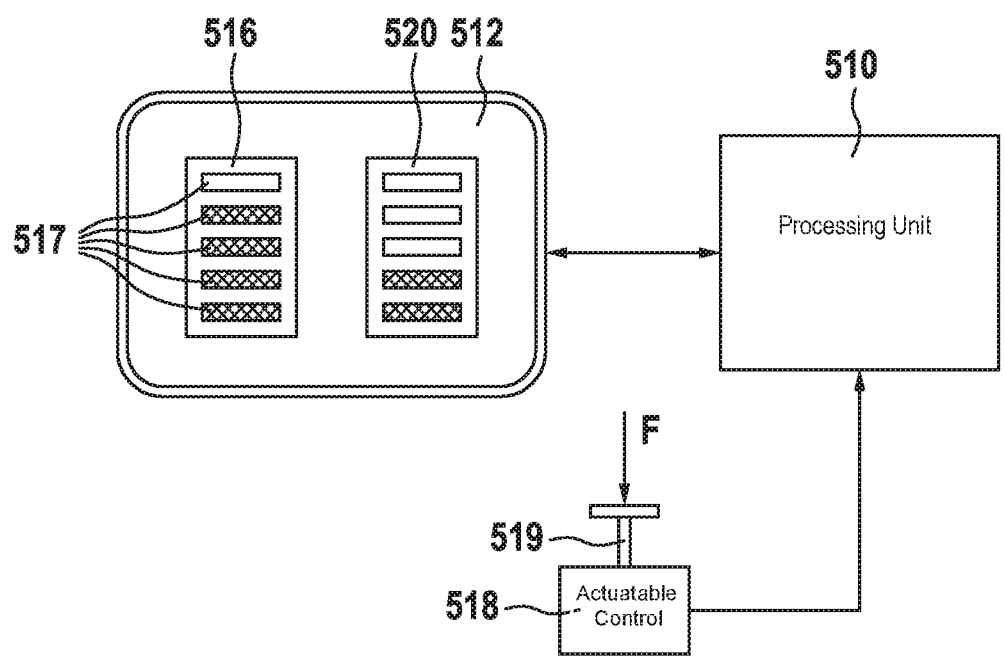
FIG. 5 shows a fifth embodiment of a monitoring device with a combined display unit/input device in the form of a touch screen.

FIG. 5 shows a fifth embodiment of a device for monitoring the attention of the operator; in this case, the processing unit 510 is coupled to a display unit 512 of any kind and to a gradually actuatable control 518 functioning as an input device.

In order to monitor the attention of the operator, the processing unit 510 first randomly generates a desired value from a predetermined range, for example from 0 to 5. The processing unit 510 shows the operator this desired value on the display unit 512, prepared in a quantitative, graphic fashion in the form of a segmented bar graph 516.

In FIG. 5, the bar graph 516 is shown in the left region of the display unit 512 and is composed of five segments 516, the lowest four of which are depicted as dark and the uppermost of which is depicted as light. Thus the randomly determined desired input is displayed to the operator as graphic information in the form of a bar graph 516.

The operator can then perform an input within the predetermined time window by means of a gradually actuatable control 518, which, in the exemplary embodiment, is configured in the form of a pressure-detecting element that can be actuated by exerting an actuating force "F" on a key 519. The actuating element 518 differs from a conventional input key of the kind in the keyboard in FIG. 1 or FIG. 3 in that the actuating element 518 is able to detect the actuating force F exerted by the operator in a sufficiently gradual way, at least for the purposes required here, in the present case divided into at least 5 steps.

The mechanically predetermined input range of the actuating element 518 from 0 (no actuation) to a maximum value of 5 (maximum force that can be exerted) is indicated in accordance with the segmentation of the graph bar 516, which indicates the desired input, on an identically configured graph bar 520 on the right side of the display unit 512.

If the operator begins to press the pushbutton 519 of the control 518, then the pressure that is currently being exerted by the operator is reported back to the operator by means of the display bar 520. The operator therefore receives an optical feedback for the pressure he is exerting with the key 519.

Within the predetermined time window for a positive feedback, the operator must adapt the pressure exerted on the key 519 so that the graph bar 516 representing the desired input and the one representing the actual input currently being exerted by the operator, which is represented by the graph bar 520, match.

If within the predetermined time window, the processing unit determines that the actual input by the operator corresponds to the desired input, then this is once again evaluated as a positive indication for the attention of the operator.

For better feedback to the operator, the processing unit 510 can be configured to optically change the graphic depiction of the bar 520 in a way that is clearly recognizable to the operator as soon as the exerted pressure on the key 519 corresponds to the actual input of the desired input. The operator must then maintain this state for a second short predetermined time period in order to trigger a positive input. This prevents an input by the operator from randomly corresponding to the desired input.

As described above, the exemplary embodiment can be modified so that the display unit 512 is a touch screen and the control 518 is implemented by means of the touch-sensitive surface of the touch screen. In order to input a response, the operator then touches the display unit 512 functioning as an input element. The input is then carried out by controlling the bar 520 by executing a gesture such as a swiping or dragging on the surface of the display unit 512 with a finger. Otherwise, the operational procedure and the function are as described above in relation to FIG. 5.

In the embodiments in FIGS. 2, 4, and 5, it is basically not possible for the operator to execute a digitally distinguishable correct or incorrect input. As explained above in connection with the embodiment in FIG. 4, this can fall within a tolerance range that can be defined in a sufficiently precise manner by means of experiments.

In a way similar to the one described above in connection with the embodiment in FIG. 5, a modification can include an intensified feedback of current comparison results of the current actual input to the desired input.

If the operator pays close attention to a feedback from the processing unit when making his input, then he can adjust his input within a predetermined input time window. For example, such an adjustment can be carried out by changing the contact point of the finger on a touch screen functioning as the input device (see FIG. 2 and FIG. 4 as well as the described possible modification to FIG. 5) and by changing the actuation of an actuating element (see FIG. 5).

A correction possibility of this kind does not negatively affect the purpose of the monitoring device since the taking into account of this type of feedback to the operator can also be evaluated as an indicator for the attention of the operator.

A feedback to the operator can take place via the display unit by means of an intuitively understandable color change, for example from red to green, possibly by way of yellow, in arbitrary steps that serve as an indication for the current deviation between the desired input and the actual input. Based on optical feedback information, the operator can then adjust the current actual input so that a "correct" input is achieved within the predetermined time window. This avoids unnecessary false alarms and exerts a motivating influence on the operator to correct his own actual input as needed.

Figure 6:
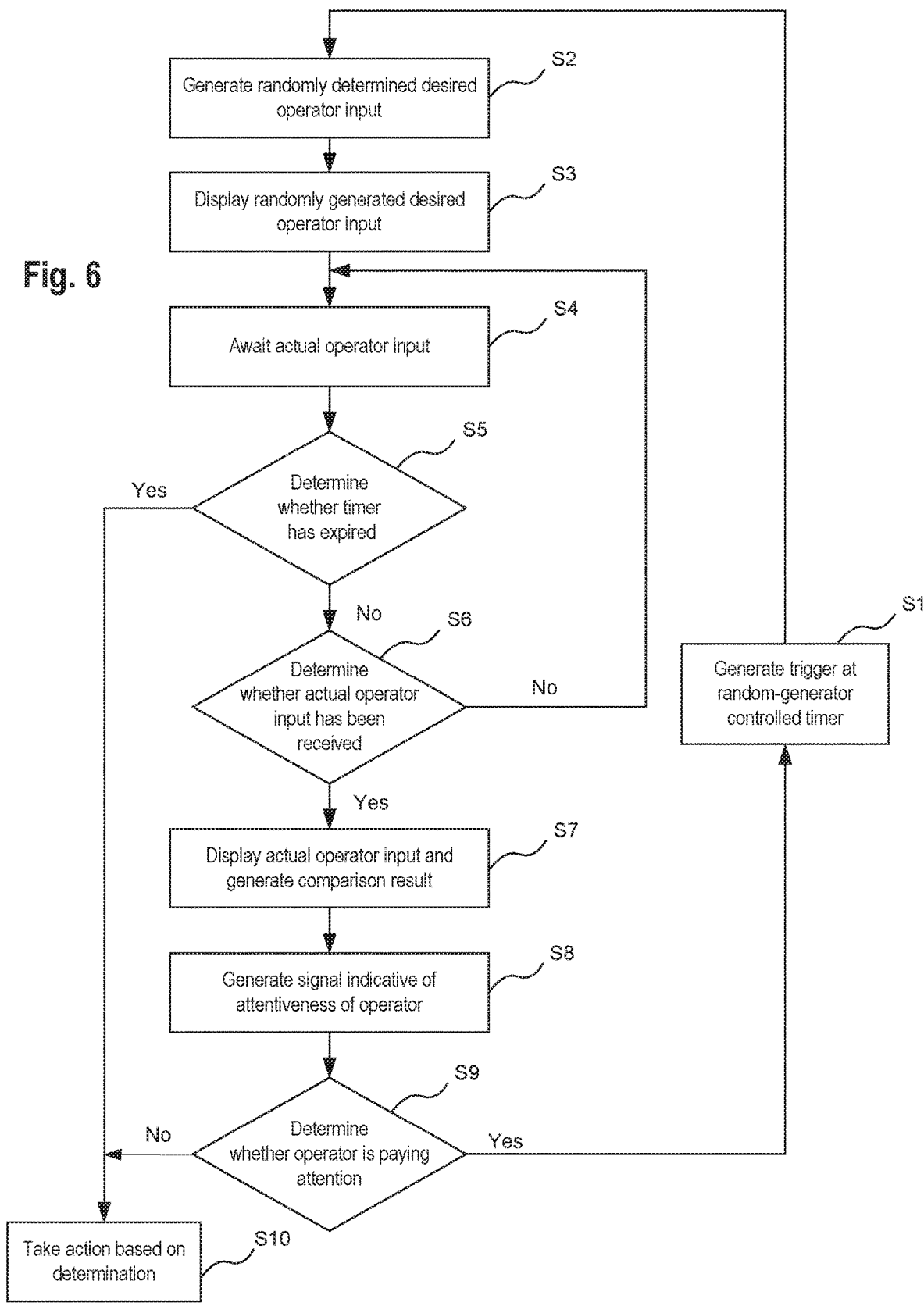
FIG. 6 shows a flow chart of an embodiment of a monitoring method.

FIG. 6 shows a flow chart of an embodiment of a monitoring method implemented by means of one of the devices explained above in connection with FIGS. 1 through 5.

In a step S1, for example by means of a random generator, the triggering of the monitoring method is initiated at irregular time intervals. This can take place, for example, by means of a random generator-controlled timer, which after going through a respective interrupt, triggers the execution of the monitoring method.

As soon as the monitoring method has been triggered by the timer in step S1, the sequence proceeds to step S2 in which information is generated that defines a randomly determined desired input for the operator.

Then the method proceeds to step S3 in which the randomly determined desired input is shown to the operator. Together with the display of the information to the operator, another predetermined timer is started, which defines the time window within which an input must be made by the operator.

After step S3, the method proceeds to step S4 in which a possible input by the operator is detected in the input device.

From step S4, the method proceeds to step S5 in which a check is performed as to whether the timer that has been started for the input time window has already expired or not. If the timer has already expired, then a negative evaluation of the operator's attention is issued and the method stops at this point and skips to step S10, which will be explained in greater detail below. If the timer has not yet expired, then the method proceeds from step S5 to step S6 in which a check is performed as to whether or not the operator has performed an input. If no input has been made by the operator, then the method returns from step S6 to step S4.

If an input by the operator has been made, then the method proceeds from step S6 to step S7 in which the detected actual input by the operator, as the response to the desired input displayed, is compared to the desired input and a comparison result is generated.

Then the method proceeds from step S7 to step S8, in which based on the desired input and the actual input, particularly based on the comparison result, a signal that indicates the attention of the operator is generated for further use.

Then the method proceeds from step S8 to step S9, in which a check is performed as to whether or not the operator is paying attention. If the signal that indicates that the operator is paying attention shows that the operator is in fact paying attention, then the method returns from step S9 back to step S1 and is restarted from there after the random-generated triggering.

If it is determined in step S9 that the operator is not paying attention, then the method proceeds from step S9 to step S10. In step S10, the signal that indicates that the operator is paying attention used as the basis for additional measures as follows.

First, an alarm can be triggered, which is intended to draw the attention of the operator back to the system or machine that the operator is supposed to be monitoring. This makes it possible, after a defined window of time since the alarm was triggered, to restart the monitoring system, for example in order to determine whether the operator is now once again paying attention. In addition or alternatively, it is also possible to trigger an alarm at a higher level, for example at a position higher than the operator. It is then possible to take further steps from there as needed.

Finally, the signal indicating the attention of the operator can also be used for direct measures to control the system or machine. For example, it is possible for the signal indicating the attention of the operator to be supplied to the system or machine via a signal input of a control unit, with the control unit bringing the system or machine into a predetermined safe state if it determines that the operator is not paying attention.

The above-explained embodiments of the monitoring system are well-suited to systems or machines in which the attention of the operator is responsible among other things for the processing results of the machine or system. For example, the monitoring device and/or monitoring method can be used in an X-ray inspection system for nondestructive inspection of objects such as luggage items at an airport checkpoint, which is continuously supplied with luggage items, and an operator must examine transmission images of the luggage items. In this case, the operator's undivided attention is required since the inspection of the luggage items does not take place in a fully automated way, but instead, the inspection results largely also depend on the experience brought to bear by the operator. The operator's attention can be randomly, but regularly monitored with the above-described monitoring device and/or monitoring method.

The invention claimed is:

1. A method for monitoring the attention of an operator of an X-ray inspection system, the X-ray inspection system configured to nondestructively inspect at least one object, the method comprising:
    displaying a randomly generated desired operator input on
        a display unit of a workstation of the X-ray inspection system and displaying X-ray inspection imaging only for the at least one object nondestructively inspected by the X-ray inspection system, the displayed desired operator input corresponding to a randomly selected position on the display unit;

determining whether an actual operator input responsive to the displayed desired operator input has been received via a user input device of the workstation of the X-ray inspection system at a processor of the workstation of the X-ray inspection system, the actual operator input including, at least in part, a corresponding operator input position on the display;

comparing the received actual operator input with the desired operator input based on the determination at the processor of the workstation of the X-ray inspection system, the comparison including matching the corresponding operator input position on the display with the randomly selected position on the display unit, the desired operator input indicated on the display unit and the received actual operator input received via the user input device needing to match to be deemed a correct attentive response by the processor of the workstation of the X-ray inspection system; and generating a signal indicative of attentiveness of the operator based on the comparison at the processor of the X-ray inspection system, an inattentive signal generated when there is not a correct attentive response, the inattentive signal triggering a command to bring the system into a predetermined safe state, the predetermined safe state including a stoppage in actuation of the X-ray inspection system.

2. The method according to claim 1, further comprising:
determining as to whether the actual operator input is received within a predetermined time following the display of the desired operator input.

3. The method according to claim 1, further comprising:
displaying the randomly generated desired operator input quantitatively in one of a graphical format and an alphanumeric format;
receiving the actual operator input via an actuation device; and
comparing the actual operator input received via the actuation input device to the desired operator input.

4. The method according to claim 3, further comprising:
displaying the actual operator input received via the actuation input device on the display unit.

5. A device for monitoring the attention of an operator of an X-ray inspection system, the X-ray inspection system configured to nondestructively inspect at least one object, said device including:
a processing unit configured to randomly generate a desired operator input;
a display unit communicatively coupled to the processor and configured to display the randomly generated desired operator input, the displayed desired operator input corresponding to a randomly selected position on the display unit, the processing unit and the display unit together configured to display X-ray inspection imaging only for the at least one object nondestructively inspected by the X-ray inspection system; and
an input device communicatively coupled to the processor and configured to receive an actual operator input responsive to the display of the desired operator input, the actual operator input including, at least in part, a corresponding operator input position on the display, and
wherein the processing unit is further configured to:
compare the received actual operator input with the desired operator input, the comparison including matching the corresponding operator input position on the display with the randomly selected position on the display unit,
generate a signal indicative of attentiveness of the operator based on the comparison, and
issue a command to a control unit of the X-ray inspection system to place the X-ray inspection system in a pre-determined safe state based on the comparison, the predetermined safe state including a stoppage in actuation of the X-ray inspection system.

6. The device according to claim 5, wherein the processing unit is further configured to determine whether the actual operator input is received within a predetermined time interval following the display of the desired operator input.

7. The device according to claim 5, wherein the display unit comprises a screen and the input device comprises a keyboard.

8. The device according to claim 5, wherein the processing unit is further configured to:
display randomly generated desired operator input in one of graphical format and an alphanumeric format,
receive the actual operator input via an actuation input device, and
compare the actual operator input received via the actuation input device to the desired operator input.

9. The device according to claim 8, wherein the processing unit is further configured to display the actual operator input via the actuation input device in one of a graphical format and an alphanumeric format on the display unit.

10. The device according to claim 5, wherein the input device comprises an actuating input device that can be gradually actuated to generate the actual operator input.

11. The device according to claim 10, wherein the actuating input device comprises:
a pressure sensor; and
an actuating element coupled to the pressure sensor configured to generate actual values associated with the actual operator input from a predetermined value range.

12. The device according to claim 5, wherein the display unit and input device comprise at least one of a touch-sensitive screen and a keypad.

* * * * *